United States Patent [19]
Voith

[11] Patent Number: 5,840,036
[45] Date of Patent: Nov. 24, 1998

[54] BLOOD PRESSURE MEASURING APPARATUS

[75] Inventor: Paul Richard Voith, Milwaukee, Wis.

[73] Assignee: Marquette Electronics, Inc., Milwaukee, Wis.

[21] Appl. No.: 810,425

[22] Filed: Mar. 4, 1997

Related U.S. Application Data

[62] Division of Ser. No. 377,628, Jan. 25, 1995, Pat. No. 5,649,535.

[51] Int. Cl.$^6$ ........................................................ A61B 5/02
[52] U.S. Cl. ............................ 600/493; 600/500; 600/485
[58] Field of Search ............................ 128/672, 677–683, 128/686–688, 691, 639, 644; 600/485, 490–496, 499–501, 372, 392

[56] References Cited

U.S. PATENT DOCUMENTS

| | | | |
|---|---|---|---|
| 3,552,385 | 1/1971 | Janssen | 128/2.05 |
| 3,885,551 | 5/1975 | Massie | 128/2.05 |
| 4,313,445 | 2/1982 | Georgi | 128/680 |
| 4,592,365 | 6/1986 | Georgi | 600/493 |
| 4,660,566 | 4/1987 | Palti | 128/677 |
| 4,800,892 | 1/1989 | Perry et al. | 128/677 |
| 4,953,557 | 9/1990 | Frankenreiter et al. | 128/677 |
| 5,031,630 | 7/1991 | Hirano et al. | 128/680 |
| 5,040,540 | 8/1991 | Sackner | 128/672 |
| 5,050,613 | 9/1991 | Newman et al. | 128/670 |
| 5,095,912 | 3/1992 | Tomita | 128/672 |
| 5,381,789 | 1/1995 | Marquardt | 128/202.25 |
| 5,381,794 | 1/1995 | Tei et al. | 128/662.03 |
| 5,381,795 | 1/1995 | Nordgren et al. | 128/663.01 |
| 5,381,796 | 1/1995 | Pompei | 128/664 |
| 5,381,797 | 1/1995 | Pak et al. | 128/687 |
| 5,381,798 | 1/1995 | Burrows | 128/696 |
| 5,381,803 | 1/1995 | Herleikson et al. | 128/708 |
| 5,381,804 | 1/1995 | Shambroom | 128/731 |
| 5,392,781 | 2/1995 | Phillips et al. | 600/493 |
| 5,551,437 | 9/1996 | Lötscher | 128/672 |
| 5,649,535 | 7/1997 | Voith | 600/493 |

*Primary Examiner*—Jennifer Bahr
*Assistant Examiner*—Bryan K. Yarnell
*Attorney, Agent, or Firm*—Michael Best & Friedrich LLP

[57] ABSTRACT

A blood pressure measuring system includes a transducer having first and second sensors adapted to be mounted above the artery of a patient with the second sensor more distal relative to the direction of blood flow than the first sensor. A processor digitizes the signals from the first and second sensors and determines when the second signal is phase shifted about 90 degrees relative to the first signal for determining the occurrence of the Korotkoff sound. The transducer comprises a film of a material having piezoelectric properties and at least two spaced apart electrodes on one surface of the film and a third electrode on the opposite side and opposed to the two electrodes.

14 Claims, 4 Drawing Sheets

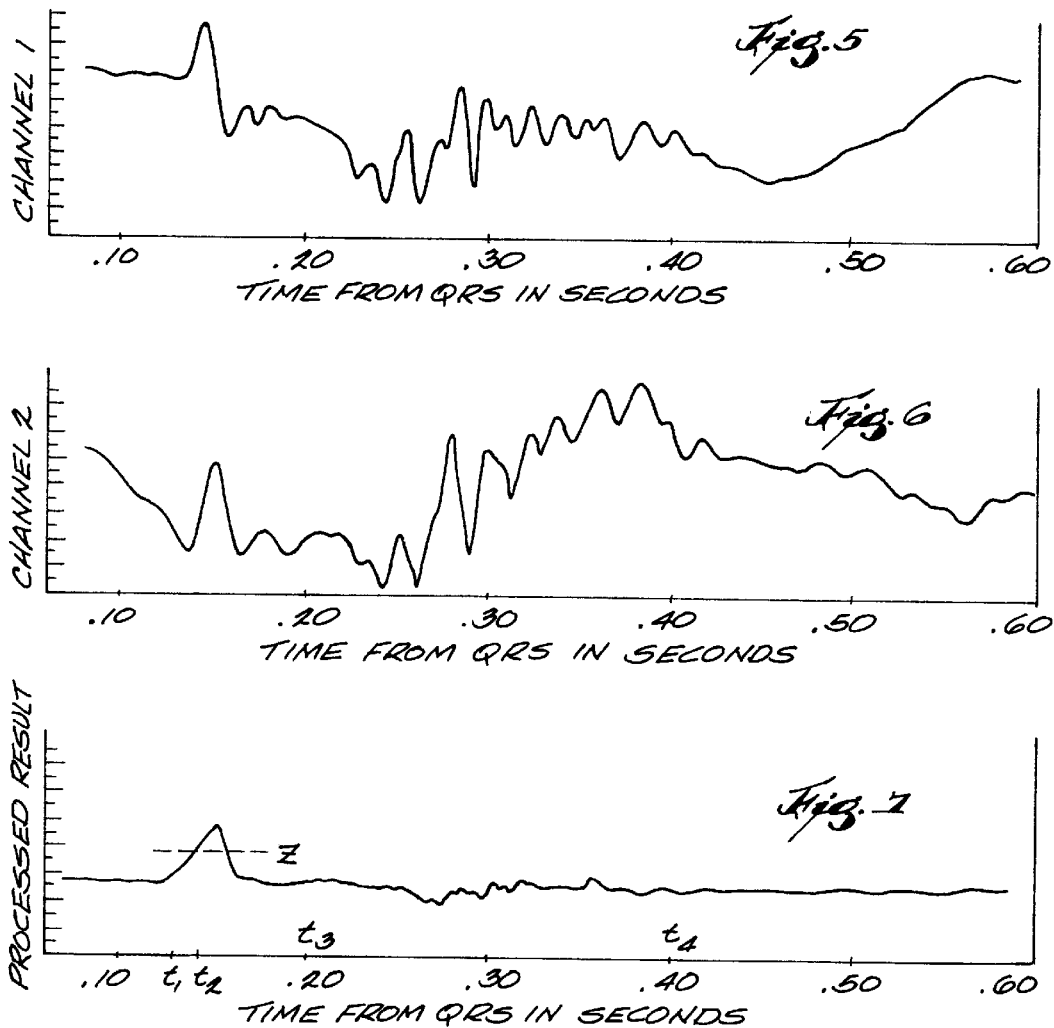

BLOOD PRESSURE MEASURING APPARATUS

This is a divisional of application Ser. No. 08/377,628, Jan. 25, 1995, entitled BLOOD PRESSURE MEASURING METHOD AND APPARATUS, now U.S. Pat. No. 5,649,535.

BACKGROUND OF THE INVENTION

This invention relates to blood pressure measuring methods and apparatus.

During each heart beat, human blood pressure normally rises from about 80 mm of mercury, called diastolic pressure, to about 120 mm of mercury, called systolic pressure. One common method of measuring these pressures, is to inflate a cuff encircling the patient's arm to a pressure above the individual's systolic pressure normally, about 140 mm of mercury, so that the patient's artery is collapsed and no blood flows. The pressure in the cuff is then gradually reduced to a pressure below the patient's systolic pressure, so that the artery opens and blood flow commences. This pressure is noted as the patient's systolic pressure. A contact microphone or other sensor is used to detect the commencement of arterial blood flow which occurs when the patient's blood pressure exceeds that of the cuff. The signal detected by the contact microphone is commonly called the Korotkoff "sound," although the signal power is normally below audible frequencies, that is, about 20 Hz. There is some difference of opinion as to whether the Korotkoff "sound" is generated by the opening of the artery which was previously compressed by the occluding cuff or the actual commencement of blood flow. As the pressure within the artery falls between heart beats, the artery is again occluded. This continues until the cuff pressure falls below the diastolic pressure in which case, the artery remains open. The pressure at the point where the Korotkoff "sound" ceases is the measurement of the patient's diastolic pressure.

One of the problems encountered with prior art blood pressure measuring systems is that in addition to the Korotkoff sound, contact microphones and other sensing devices also detect noise signals which may result from any number of causes, such as muscular contractions and the like. One prior art method of attempting to compensate for noise signals is to employ a pair of sensors one of which is located proximal and the other distal relative to the heart. Each sensor detects the Korotkoff signal plus noise signals. The signals in the two sensors are subtracted which can have the effect of doubling the Korotkoff signal strength relative to random noise and even eliminate common mode noise but has the disadvantage of also passing any portion of the noise which is not of identical magnitude in both sensors.

SUMMARY OF THE INVENTION

It is the primary object of the invention to provide a new and improved blood pressure measuring process and apparatus.

A further object of the invention is to provide a blood pressure measuring method and apparatus which accurately identifies the occurrence of Korotkoff sounds.

Another object of the invention is to provide a blood pressure measuring method and apparatus in which the effect of noise signals is minimized.

A still further object of the invention is to provide a new and improved signal transducer for blood pressure measuring apparatus.

Yet another object of the invention is to provide a transducer for blood pressure measuring devices which can readily be mounted in an occluding cuff.

These and other objects and advantages of the present invention will become more apparent from the detailed description thereof taken with the accompanying drawings.

In general terms, the invention comprises a transducer for use in a blood pressure measuring system including means for applying pressure to the artery for preventing blood flow, and means for gradually reducing the pressure on the artery whereby blood flow commences when the pressure applied to the artery falls below the patient's systolic pressure. The transducer is constructed and arranged to be applied to a patient in an opposed relation to an artery and includes first and second responsive means for generating a signal in response to the initiation of blood flow, support means for the first and second responsive means for positioning the first responsive means proximal and the second responsive means distal relative to the direction of blood flow in the artery, and processing means is connected to the first and second responsive means for determining when a signal in the second responsive means is phase shifted relative to the corresponding signal in the first responsive means. The transducer according to the preferred embodiment comprises a thin film of a material having piezoelectric properties and at least a pair of spaced electrodes on one surface and at least one electrode on the opposite surface and opposed to the pair of electrodes.

According to another aspect, the invention comprises a blood pressure measuring method comprising the steps of applying pressure to the artery of a patient to arrest the flow of blood therein, gradually reducing the pressure on the artery below that of the blood pressure therein, sensing first and second signals occurring as a result of the commencement of blood flow in first and second spaced apart locations in the artery of the patient wherein the second location is more distal relative to the direction of blood flow than the first location, and determining when the second signal is phase shifted relative to the first signal.

BRIEF DESCRIPTION OF THE INVENTION

FIG. 1 schematically illustrates a blood pressure sensing system according to the invention;

FIGS. 5 and 6 show the same signals as in FIGS. 2 and 3 except that the patient is walking on a treadmill;

FIG. 7 shows a signal derived from the signals of FIGS. 5 and 6;

Figure 1:
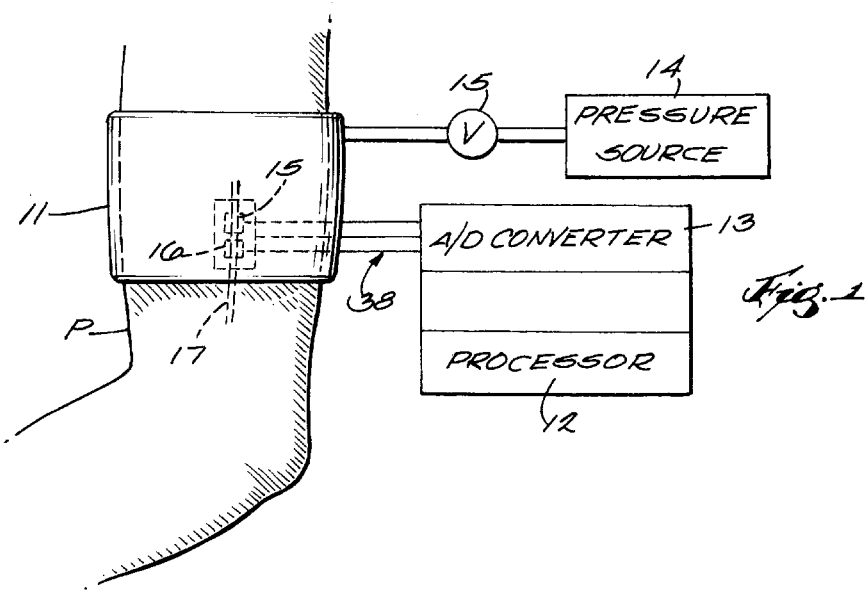
Figure 8A:
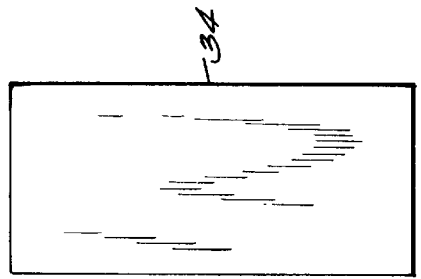
Figure 8C:
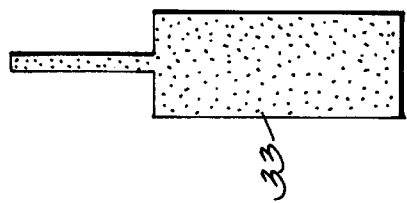
Figure 8D:
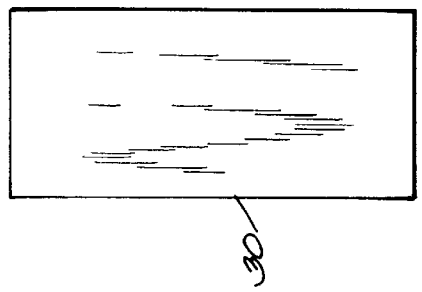
Figure 8B:
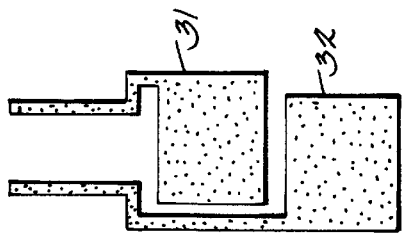
Figure 8A:
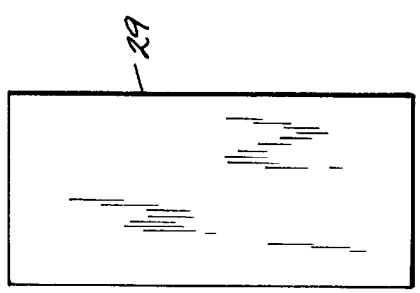
Figure 9:
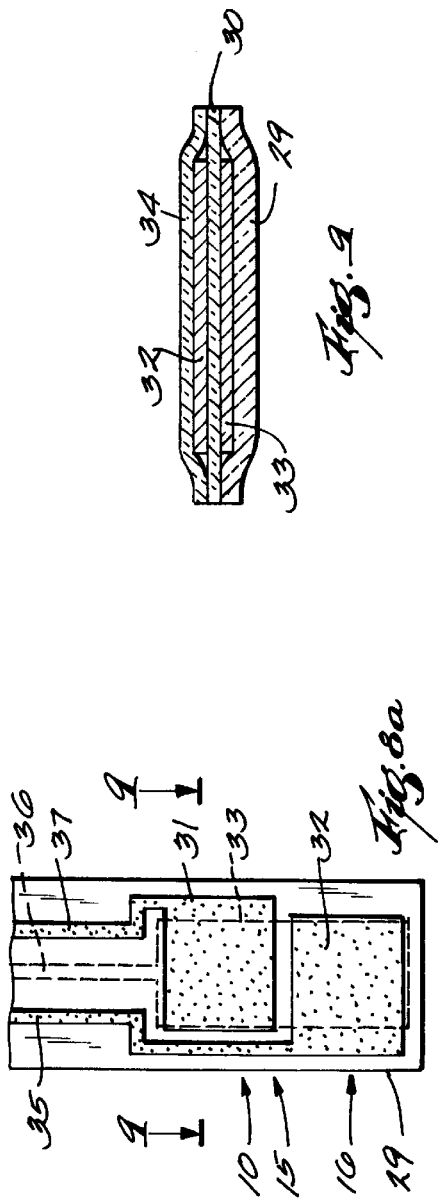
Figure 12:
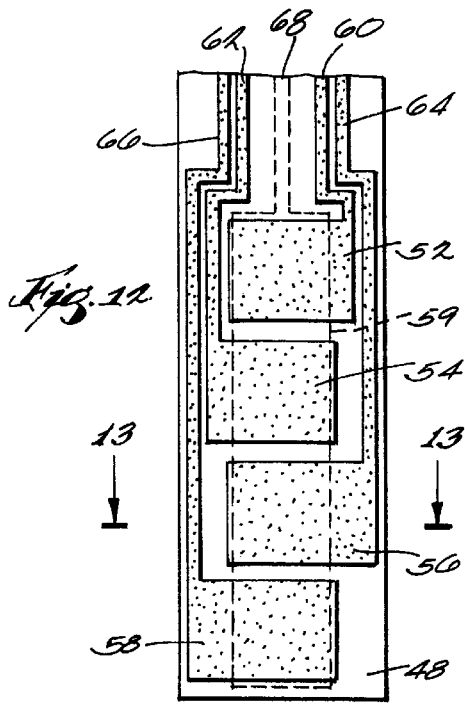
Figure 13:
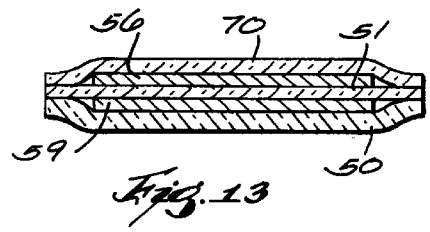
Figure 11:
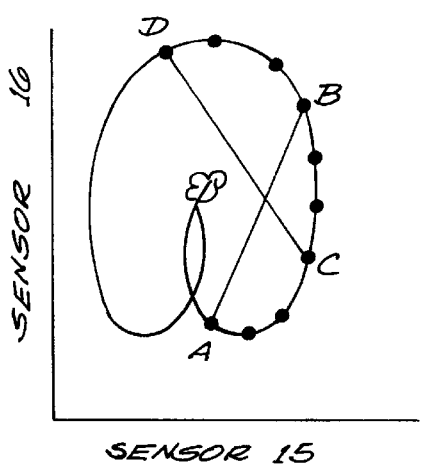
Figure 10:
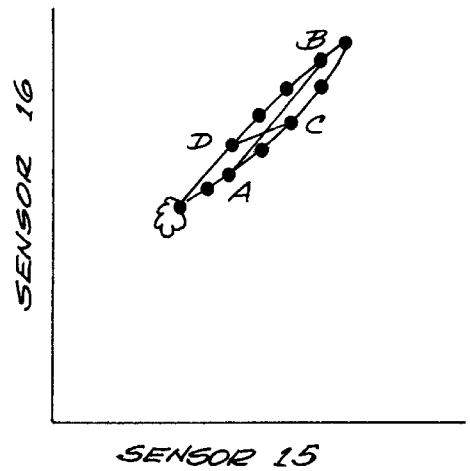

FIGS. 8a, 8b, 8c, 8d, 8e, and 8f show a transducer for use in the system of FIG. 1 according to a first embodiment of the invention;

FIG. 9 is a view taken along lines 9—9 of FIG. 8;

FIG. 10 shows a plot of the digitized signal from the system of FIG. 1 plotted on an X-Y axis in the absence of a Korotkoff sound;

FIG. 11 shows a plot of the digitized signal from the system of FIG. 1 during the occurrence of a Korotkoff sound;

FIGS. 12 and 13 show a transducer for use in the system of FIG. 1 according to the preferred embodiment of the invention; and FIG. 13 is a view taken along lines 13—13 of FIG. 12.

DETAILED DESCRIPTION OF THE PREFERRED EMBODIMENTS

The pressure measuring system according to the invention is shown in FIG. 1 to include a dual low frequency transducer 10 which is mounted on a pressure cuff 11 and coupled to a processor 12 which includes an analog to digital converter 13. The pressure cuff 11 is conventional and will not be described in detail for the sake of brevity. It will be sufficient for the purpose of understanding the invention to state that the cuff 11 comprises a bladder constructed and arranged to be mounted on the arm P of a patient in a conventional manner. A pressure source 14 is connected to the cuff 11 for inflating the cuff to a pressure above the patient's systolic pressure and means, symbolized by a valve V, is provided for gradually reducing the pressure in cuff 11 to below the patient's diastolic pressure. The pressure source 14 and the valve V may be conventional and will not be discussed in detail for the sake of brevity.

The transducer 10 includes a pair of spaced apart sensors 15 and 16 for simultaneously sensing the Korotkoff sound at two different positions over the patient's brachial artery 17, one position being more proximal than the other relative to the direction of blood flow and preferably under the distal portion of the occluding cuff 11.

It has been found that the signal morphology associated with the Korotkoff sound appears in each sensor 15 and 16, but is delayed in the channel of the distal sensor 16. The delay is about 1 millisecond per millimeter of separation. The smaller the separation, the more similar the morphology. Separations of about 12 millimeters provides similar signals with measurable time separations of about 6–18 milliseconds. However, most noise portions of the signals do not have a significant time delay but are substantially coincident for both sensors 15 and 16. As will be discussed more fully below, the processor 12 digitizes and then determines the existence of phase separation of the signals from sensors 15 and 16 to identify the occurrence of the Korotkoff sound with minimal noise interference.

By observation, it is estimated that the main frequency characteristic of the Korotkoff signal is about 20 Hz. (±50%). This frequency estimate along with the measured delay per unit separation of the sensors 15 and 16 permits the calculation of a wavelength of 50 millimeters so that the optimal spacing of the sensors 15 and 16 is in the order of one-quarter wavelength or about 12.5 millimeters.

It is assumed that for cuff pressures between systolic and diastolic, each pulse causes the artery 17 to open at the proximal end of the cuff 11 first with more distal portions of the artery opening later in time as the mass of blood transits the artery below the cuff. It is this sudden expansion of the artery wall and the passage of the blood mass which is detected first by the sensor 15 and then after a time delay by the sensor 16.

Figure 2:
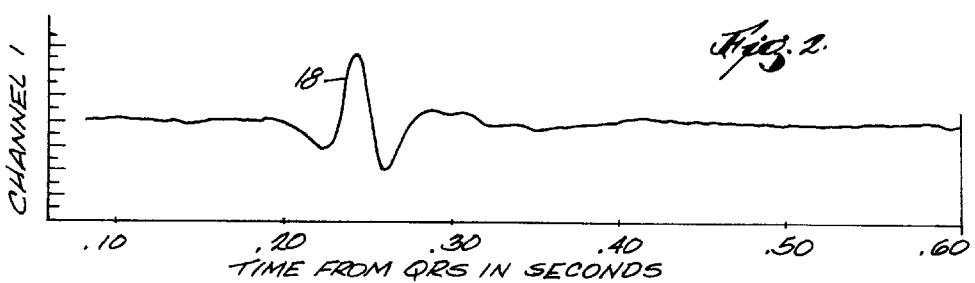
FIGS. 2 and 3 show digitized signals sensed by a blood pressure measuring apparatus of FIG. 1.
Figure 3:
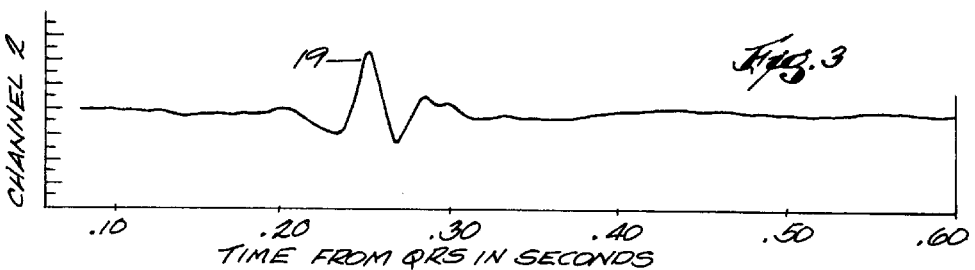
Figure 4:
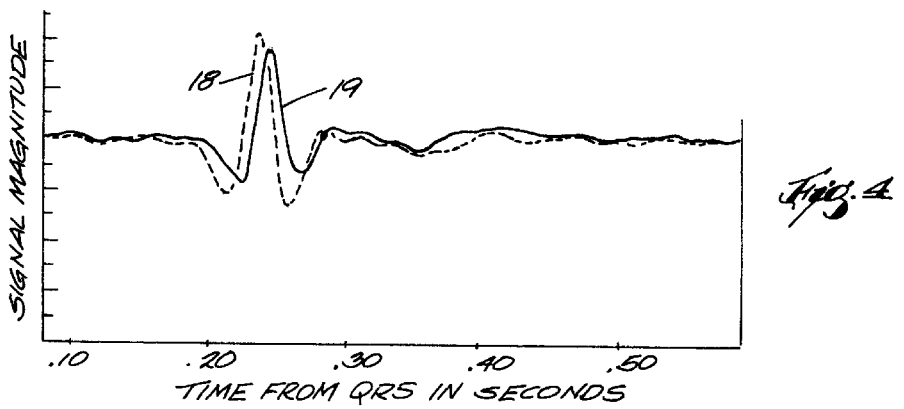
FIG. 4 shows the signals of FIGS. 2 and 3 superimposed.

FIGS. 2 and 3 show the digitized signals from sensors 15 and 16, respectively, and FIG. 4 shows the digitized output from the sensors 15 and 16 with the two channels superimposed. The time scale is in seconds from the previous heart beat and spans about one-half second. The cuff pressure is between systolic and diastolic for the subject which is seated and quiet. A first trace 18, derived from sensor 15, and a second trace 19, derived from sensor 16, are shown in FIG. 4 with the images of the Korotkoff signal morphology centered at about 0.25 seconds. The delay between the two Korotkoff signal morphologies is clearly evident.

FIGS. 5 and 6 are similar to FIGS. 2 and 3 except that the subject is walking at 3.3 miles per hour on a treadmill. In both FIGURES, the actual Korotkoff signal occurs between 0.1–0.2 seconds in the time scale. The remaining portions of the signal are motion artifact which for a substantial portion of the time period is equal to or greater in magnitude than the Korotkoff signal. FIG. 7 shows the signal 20 which is derived from a phase comparison of the signals of FIGS. 5 and 6 in the manner discussed below. It can be seen that signal 20 peaks during the Korotkoff signal while the remaining portion of the signal is relatively flat during the motion artifact even though the artifact is of similar magnitude and frequency. Thus, by employing two signals separated in time it is possible to identify low frequency Korotkoff signals even in an ambulatory environment where the noise portion of the signal is substantial.

FIG. 8a is a top-plan view of the transducer 10 in accordance with a first embodiment of the invention, FIGS. 8b, 8c, 8d, 8e and 8f show the various components which form the transducer 10 and FIG. 9 is a cross section thereof. In particular, the transducer 10 is disposed on a generally rectangular substrate 29 which may comprise a film of a material, such as Mylar, and which has a thickness of about 5 mils. The transducer includes a film 30 of a material which has piezoelectric properties, i.e., its polarity changes with changes in mechanical stress. One material exhibiting these properties is piezo electric polyvinylidene fluoride (PVDF). The piezoelectric film 30 preferably has a thickness of about 28 microns. On the upper surface of the piezoelectric film 30 is a pair of electrodes 31 and 32 which may comprise a silver ink which is printed or silk screened on the film 30. On the lower surface of the film 30 there is a ground electrode 33 which may also be a silver ink. The piezoelectric film 30, with the electrodes 31, 32 and 33, is suitably laminated to the substrate 29 with the ground electrode 33 disposed between the substrate 29 and the film 30. A protective layer 34 of film, such as Mylar, and about 1–2 mils. thick is laminated to the film 30 above the electrodes 31 and 32. It will be appreciated that in the cross-sectional view of FIG. 9, the thicknesses of the components are exaggerated for purposes of illustration. It will also be appreciated that while a single ground electrode 33 is illustrated, separate ground electrodes respectively disposed in an opposed relation to electrodes 31 and 32 may also be employed.

The sensor 15 comprises the portions of electrodes 31 which overlap the ground electrode 33 and that portion of the piezoelectric film 30 therebetween and sensor 16 similarly comprises the overlapping portions of electrodes 32 and 33 and the portion of piezoelectric film therebetween. The sensors 15 and 16 generate a voltage signal when there is a change in the stress in the film 30

The overlapping areas of electrodes 31 and 32 with electrode 33 should be of a size sufficient to generate a detectable electrical signal upon the occurrence of the Korotkoff sound, taking into consideration the desired spacing between the sensors 15 and 16 which, as indicated above, is preferably about one-quarter wave length of the dominant signal frequency. As a result, the Korotkoff sound is detected in both sensors, but detection in the distal sensor 16 is time delayed relative to that in the proximal sensor 15. Because the sensors are in close proximity, the frequency components of the noise which are within the signal band, i.e., 10–40 hz., tend to have a similar phase in both sensors, that is, they correlate with zero delay. The delay in the pick-up of the Korotkoff sound between the sensors 15 and 16 permits the Korotkoff signals to be differentiated from the noise. If the sensors 15 and 16 are spaced too far apart, the noise signal may become uncorrelated. On the other hand, if the sensors 15 and 16 are too close, it is more difficult to differentiate the Korotkoff signals. The optimal distance for correlating the noise signals while still permitting differentiation is about one-quarter wave length.

In the embodiment shown in FIGS. 8a–8f the active area of the sensors 15 and 16 are about 10 mm. square and the distance between the sensors is about 1 mm. so that the center-to-center distance is about 11 mm. or about one-quarter wave length. While the active areas of the sensors 15 and 16 are shown to be square, they may have any shape, although the configuration illustrated permits the transducer 10 to be more compact than other conventional shapes. The electrodes 31 and 32 and the ground electrode 33 are connected by conductive strips 35, 36 and 37, respectively, to processor 12 through a suitable cable 38 as seen in FIG. 1.

In operation, a pressure wave is produced either by the opening of the artery or the commencement of blood flow when the pressure in the artery 17 exceeds that in the cuff 11. This pressure wave slightly distorts the piezoelectric film 30, first in the sensor 15 and then in sensor 16 after a time delay. As the piezoelectric film distorts 30, a voltage signal is produced which is transmitted by conductors 35, 36 and 37 to the processor 12. The processor 12 includes an analog to digital converter 38 which digitalizes the analog voltage signals from the sensors 15 and 16.

FIG. 10 shows a plot of the digitized signals from the sensors 15 and 16 plotted with X being the digitized signals on sensor 15 and Y being the digitized signals on sensor 16. Between $t_3$ and $t_4$ of FIG. 7, the signals in the two sensors are relatively in phase. As a result, the plot of the digitized signals shown in FIG. 10, generally comprises a straight line or a relatively flat oval. Assuming that, at time $t_1$, the cuff pressure is between the diastolic and systolic pressures, the proximal sensor 15 begins to sense the Korotkoff sound and at time $t_2$ which is one-quarter wave length later, the distal sensor 16 begins to sense the Korotkoff sound. These signals are generally sinusoidal, and as a result of the one quarter wave length spacing of sensors 15 and 16, are 90° out of phase. During the occurrence of the Korotkoff sound, the X-Y plot of the digitized signals from sensors 15 and 16 becomes more circular as shown in FIG. 11.

The processor 12 determines when the signals from sensors 15 and 16 are out of phase to identify the occurrence of the Korotkoff sound. In the preferred embodiment of the invention, this is accomplished by calculating the cross-product of vectors which intersect sampling points plotted on the X-Y axes and time delayed about 0.015 seconds using the following expression:

$$R=(X_{i+b}-X_i)(Y_{i+c}Y_{i+a})-(X_{i+c}-X_{i+a})(Y_{i+b}Y_i).$$

Where:

$X_i$ is a sample from the sensor 15, $Y_i$ is a sample from sensor 16.

a is signal delay divided by sample time.

b is one-half signal period.

c is a+b.

The cross-product R of the vectors AB and CD is shown in FIG. 10. During the period $t_3$–$t_4$, when the plot is a straight line or a relatively flat oval, R is relatively low and less then the threshold value Z as seen in FIG. 7. At time $t_1$, the proximal sensor 15 begins to sense the Korotkoff sound and at time $t_2$, the distal sensor 16 begins to sense the Korotkoff sound. The Korotkoff signals in sensors 15 and 16 are generally sinusoidal and one-quarter wave length apart or 90° out of phase. As a result, the X-Y plot of these signals becomes more circular, as shown in FIG. 10. The cross product of the vectors AB and CD thus increases during the Korotkoff signal as shown in FIG. 7. The processor 12 compares the computed value R to the threshold value Z to indicate the occurrence of the Korotkoff sound. The pressure in the cuff at time $T_1$ when the Korotkoff sound is first sensed is the patient's systolic pressure.

As the pressure in cuff 11 is decreased gradually to a level below systolic pressure, the Korotkoff sound is sensed during each heart beat. When the patient's blood pressure equals or exceeds that in cuff 11, so that the artery remains open between heart beats, the Korotkoff sound is no longer detected. The pressure in the cuff at this point is the patient's diastolic pressure.

FIGS. 12 and 13 show a transducer 48 according to the preferred embodiment of the invention. Here, the transducer 48 also includes a substrate 50, a piezoelectric film 51, four electrodes 52, 54, 56 and 58 applied to one surface of the film 51, and a ground electrode 59 applied to the opposite surface. Conductors 60, 62, 64, 66 and 68 respectively connect electrodes 52, 54, 56, 58 and 59 to the processor 12. A thin protective film 70 of a material such as Mylar is applied above the electrodes 52, 54, 56 and 58. In the preferred embodiment, the overlapping active areas of electrodes 52, 54, 56 and 58 with electrode 59 are each 10 millimeters square and are located one millimeter apart so that the center-to-center distance between successive electrodes 52, 54, 56 and 58 is 11 millimeters or about one-quarter wave length. In the processor 12, the signals from electrode 52 is subtracted from the signal from electrode 56 and the signal from electrode area 54 is subtracted from the electrode 58 signal. This provides two differential sensors having an effective center-to-center distance of about 11 millimeters or one-quarter wavelength. By taking the differential between the signals in the two active areas, greater signal strength is achieved. The differential signals are digitalized and then processed in the manner discussed with respect to the embodiment of FIGS. 8a–8f.

By locating the sensors one-quarter wave length apart and phase comparing the signals in the two sensors, the signal in each sensor pair related to the occurrence of the Korotkoff sound can be readily detected while the effect of the noise signals can be substantially eliminated.

While only a few embodiments of the invention have been illustrated and described, it is not intended to be limited thereby, but only by the scope of the appending claims. For example, while a specific transducer is disclosed, the invention may also be practiced with a transducer consisting of conventional sensors responsive to the Korotkoff sound and located about one-quarter wave length apart. These may include, for example, acoustic microphones, strain gauges, and the like.

I claim:

1. A transducer for use with a blood pressure measuring system having means for applying pressure to a patient's artery to arrest blood flow in the artery and for releasing the pressure wherein a signal occurs when the pressure applied by the pressure applying means is reduced sufficiently to permit the commencement of intermittent blood flow in the artery, said signal having a wavelength, said transducer including first and second signal responsive means for sensing the signal occurring upon the commencement of blood flow in the artery, said first and second responsive means being spaced apart a distance equal to about one-quarter of the wave length of the signal associated with the commencement of blood flow as the pressure on the artery is reduced.

2. The transducer set forth in claim 1 wherein the distance between said first and second responsive means is about 11 mm.

3. The transducer set forth in claim 1 wherein said transducer includes a thin, flexible film of a material having piezoelectric properties, first and second spaced apart electrodes on one surface of the film and at least one additional electrode on the opposite surface and in an opposed relation to said first and second electrodes.

4. The transducer set forth in claim 3 wherein the effective distance between said first and second electrodes is about 11 mm.

5. The transducer set forth in claim 1 wherein said signal is the Korotkoff sound and the center to center distance between said responsive means is about one-quarter of the wavelength of the Korotkoff sound.

6. A transducer for use with a blood pressure measuring system having means for applying pressure to a patient's artery to arrest blood flow in the artery and for releasing the pressure wherein a signal occurs when the pressure applied by the pressure applying means is reduced sufficiently to permit the commencement of intermittent blood flow in the artery, said signal having a wavelength, said transducer including first, second, third and fourth sensors for sensing the signal associated with the commencement of blood flow in the artery, said first, second, third and fourth sensors being successively spaced apart a distance equal to one-quarter of the wave length of the signal associated with the commencement of blood flow as the pressure on the artery is reduced.

7. The transducer set forth in claim 6 wherein the signal is the Korotkoff sound and the successive distances between said first, second, third and fourth sensors is equal to about one-quarter of the wave length of the Korotkoff sound.

8. The transducer set forth in claim 7, and wherein each of said sensors comprise a thin, flexible film of a material having piezoelectric properties, said material having opposite sides; first, second, third and fourth spaced apart electrodes on one side of said material and at least one additional electrode applied to the other side of said material and in an opposed relation to the first, second, third and fourth electrodes.

9. The transducer set forth in claim 8 and including a substrate for supporting said transducer.

10. A transducer for use in a blood pressure measuring system and comprising a thin, flexible film of a material having piezoelectric properties, said material having opposite sides, first, second, third and fourth spaced apart and aligned electrodes on one side of said material and at least one additional electrode on the other side of said film and in an opposed relation to said first, second, third and fourth electrodes, the successive distances between said first, second, third and fourth electrodes being about one-quarter of the wave length of the Korotkoff sound.

11. A transducer for use in a blood pressure measuring system having means for applying pressure to a patient's artery to arrest blood flow in the artery, and means for releasing the pressure wherein a signal occurs when the pressure exerted by the pressure applying means is reduced sufficiently to permit the commencement of intermittent blood flow in the artery, said signal having a wavelength, said transducer including a thin, flexible substrate, first and second signal sensing means for sensing the signal associated with the commencement of blood flow, said signal sensing means being spaced apart on said substrate a distance equal to about one-quarter of the wavelength of the signal.

12. The transducer set forth in claim 11, wherein the distance equals about 11 mm.

13. A blood pressure measuring device including an occluding cuff having a proximal edge and a distal edge, said pressure cuff being constructed and arranged for applying pressure to arrest blood flow in the artery of a patient and for releasing the pressure wherein the Korotkoff sound occurs in the distal portion of the cuff when the pressure released sufficiently to permit the commencement of intermittent blood flow in the artery, said Korotkoff sound having a wavelength, a transducer disposed in the distal portion of the cuff and including first and second sensors responsive to the Korotkoff sound occurring upon the commencement of blood flow in the artery, said first and second sensors being spaced apart one-quarter of the wavelength of the Korotkoff sound.

14. The blood pressure measuring device set forth in claim 13, wherein the distance between the first and second sensors is about 11 mm.

* * * * *